United States Patent [19]

Yafuso et al.

[11] Patent Number: 5,583,213

[45] Date of Patent: Dec. 10, 1996

[54] PROCESS TO ACTIVATE SULFATED POLYSACCHARIDES

[75] Inventors: Masao Yafuso, Lake Forest, Calif.; Robert J. Linhardt, Iowa City, Iowa

[73] Assignee: Minnesota Mining and Manufacturing Company, St. Paul, Minn.

[21] Appl. No.: 439,522

[22] Filed: May 12, 1995

[51] Int. Cl.⁶ .......................... C08B 37/00; C08B 37/02; C08B 37/08; C08B 37/10

[52] U.S. Cl. .......................................... 536/55.3; 536/124

[58] Field of Search ..................................... 536/55.3, 124

[56] References Cited

U.S. PATENT DOCUMENTS

| | | | |
|---|---|---|---|
| 3,475,385 | 10/1969 | Bixler et al. | 528/341 |
| 3,617,344 | 11/1971 | Leininger | 428/422 |
| 3,634,123 | 1/1972 | Eriksson et al. | 428/447 |
| 3,639,141 | 2/1972 | Dyck | 427/2.25 |
| 3,673,612 | 7/1972 | Merrill et al. | 623/2 |
| 3,755,218 | 8/1973 | Yen et al. | 428/35.5 |
| 3,766,104 | 10/1973 | Bonin et al. | 523/112 |
| 3,810,781 | 5/1974 | Eriksson et al. | 424/423 |
| 3,826,678 | 7/1974 | Hoffman et al. | 428/420 |
| 3,846,353 | 11/1974 | Grotta | 523/112 |
| 3,853,804 | 12/1974 | Yen et al. | 524/233 |
| 4,046,725 | 9/1977 | Pusineri | 523/112 |
| 4,116,898 | 9/1978 | Dudley et al. | 424/78.27 |
| 4,118,485 | 10/1978 | Eriksson et al. | 514/56 |
| 4,141,857 | 2/1979 | Levy | 502/439 |
| 4,217,338 | 8/1980 | Quash | 436/543 |
| 4,229,838 | 10/1980 | Mano | 623/1 |
| 4,239,664 | 12/1980 | Teng et al. | 525/54.2 |
| 4,265,927 | 5/1981 | Erickson et al. | 427/2.24 |
| 4,301,067 | 11/1981 | Koshugi | 536/20 |
| 4,326,532 | 4/1982 | Hammar | 604/266 |
| 4,329,383 | 5/1982 | Joh | 428/376 |
| 4,331,697 | 5/1982 | Kudo et al. | 427/2.11 |
| 4,349,467 | 9/1982 | Williams et al. | 525/54.2 |
| 4,350,806 | 9/1982 | Wagener | 528/289 |
| 4,424,346 | 1/1984 | Hall et al. | 536/20 |
| 4,521,564 | 6/1985 | Solomon et al. | 525/54.1 |
| 4,526,714 | 7/1985 | Feijen et al. | 530/363 |
| 4,565,740 | 1/1986 | Golander et al. | 428/409 |
| 4,600,652 | 7/1986 | Solomon et al. | 424/423 |
| 4,613,517 | 9/1986 | Williams et al. | 427/2.24 |
| 4,613,665 | 9/1986 | Larm | 536/20 |
| 4,642,242 | 2/1987 | Solomon et al. | 427/2.12 |
| 4,720,512 | 1/1988 | Hu et al. | 523/112 |
| 4,786,556 | 11/1988 | Hu et al. | 428/412 |
| 4,806,595 | 2/1989 | Noishiki et al. | 525/54.2 |
| 4,810,784 | 3/1989 | Larm | 536/20 |
| 4,865,870 | 9/1989 | Hu et al. | 427/2.1 |
| 4,871,357 | 10/1989 | Hsu et al. | 604/266 |
| 4,876,126 | 10/1989 | Takemura et al. | 428/35.7 |
| 4,935,204 | 6/1990 | Seidel et al. | 424/529 |
| 4,944,767 | 7/1990 | Barbucci et al. | 623/66 |
| 4,973,493 | 11/1990 | Guire | 427/2.24 |
| 4,987,181 | 1/1991 | Bichon et al. | 525/54.1 |
| 5,013,717 | 5/1991 | Solomon et al. | 514/56 |
| 5,047,020 | 9/1991 | Hsu | 604/266 |
| 5,049,403 | 9/1991 | Larm et al. | 427/2.1 |
| 5,053,048 | 10/1991 | Pinchuk | 623/1 |
| 5,061,750 | 10/1991 | Feijen et al. | 525/54.1 |
| 5,116,962 | 5/1992 | Stuber et al. | 525/54.2 |
| 5,132,108 | 7/1992 | Narayanan et al. | 424/78.17 |
| 5,145,956 | 9/1992 | Lam et al. | 536/124 |
| 5,159,050 | 10/1992 | Onwumere | 528/67 |
| 5,165,919 | 11/1992 | Sasaki et al. | 424/78.17 |
| 5,182,317 | 1/1993 | Winters et al. | 523/112 |
| 5,198,493 | 3/1993 | Holmberg et al. | 525/54.1 |
| 5,213,898 | 5/1993 | Larm et al. | 428/422 |
| 5,217,492 | 6/1993 | Guire et al. | 623/11 |
| 5,219,926 | 6/1993 | Lindman et al. | 525/54.1 |
| 5,250,613 | 10/1993 | Bergstrom et al. | 525/54.1 |
| 5,258,041 | 11/1993 | Guire et al. | 623/66 |
| 5,308,641 | 5/1994 | Cahalan et al. | 427/2.1 |

FOREIGN PATENT DOCUMENTS

| | | | |
|---|---|---|---|
| 1160548 | 1/1984 | Canada | C12Q 1/34 |
| 276814A1 | 3/1990 | Germany | B01D 15/08 |
| WO87/00060 | 1/1987 | WIPO | A61L 33/00 |
| WO88/02623 | 4/1988 | WIPO | A61F 2/43 |
| WO91/05817 | 5/1991 | WIPO | C08J 7/12 |
| WO91/16932 | 11/1991 | WIPO | A61L 33/00 |
| WO92/00747 | 1/1992 | WIPO | A61K 31/74 |
| WO93/05825 | 4/1993 | WIPO | A61L 33/00 |
| WO93/05793 | 4/1993 | WIPO | A61K 31/725 |

OTHER PUBLICATIONS

Hoffman et al., "A New Method for Covalent Coupling of Heparin and Other Glycosaminoglycans to Substrates Containing Primary Amino Groups", *Carbohydrate Research*, 117(1983) 328–331.

Larm et al., "A New Non–Thrombogenic Surface Prepared by Selective Covalent Binding of Heparin Via a Modified Reducing Terminal Residue", 1984.

Wilchek et al., "Affinity Chromatography", *Methods in Enzymology*, vol. 104, 1984, pp. 3–55.

Larm et al., "An Approach to Antithrombosis by Surface Modification", *Progress in Artificial Organs*, 1985, 313–318.

Liu et al., "New Approaches for the Preparation of Hydrophobic Heparin Derivatives", *Journal of Pharmaceutical Sciences*, vol. 83, No. 7, Jul. 1994, 1034–1039.

*Primary Examiner*—John Kight
*Assistant Examiner*—Kathleen Kahler Fonda
*Attorney, Agent, or Firm*—Gary L. Griswold; Walter N. Kirn; Paul W. Busse

[57] ABSTRACT

The present specification is directed to a novel process to prepare an activated sulfated polysaccharide which may then be used in subsequent reactions or processes to bind the reactive polysaccharide with a nucleophilic agent or an aminated surface. The activating process comprises the steps of initially forming a polysaccharide tetraalkylammonium salt by contacting an aqueous mixture of a sulfated polysaccharide salt with a cation exchange resin to give a polysaccharide free acid and then contacting the polysaccharide free acid with a tetraalkylammonium hydroxide to give the polysaccharide tetraalkylammonium salt, and subsequently forming an activated sulfated polysaccharide by contacting the polysaccharide tetraalkylammonium salt of step i) with a coupling reagent in an aprotic organic solvent at ambient temperatures for a period of time sufficient to form the activated sulfated polysaccharide.

15 Claims, 6 Drawing Sheets

FIG. 3

Step 1

SUBSTRATE + (NHCH$_2$CH$_2$NCH$_2$CH$_2$NH$_2$)$_x$
       |
       CH$_2$CH$_2$NH$_2$

Step 2

SUBSTRATE
   |
(NHCH$_2$CH$_2$NCH$_2$CH$_2$NH$_2$)$_x$
   |
   CH$_2$CH$_2$NH$_2$

Formula 7 and Formula 8

Step 3

Formulas 9-11

Formula 1

Formula 2

$R^5$=SO$_3$Na or H
$R^6$=CH$_3$CO, or SO$_3$Na or H

Formula 3

Formula 4

$R^2$=SO$_3$H or H
$R^3$=CH$_3$CO or CO$_3$H, or H

Formula 5

Formula 6

R⁷=SO₃N(R¹)₄ or H
R¹⁰=CH₃CO, or SO₃N(R¹)₄ or H

Formula 7

R⁸=CN or H

Formula 8

R⁸=CN or H
R⁹=SO₃NR₄, H or CN

Formula 9

Formula 10

Formula 11
R8=OH
R9=SO$_3$N(R1)$_4$, H
R10= —COCH$_3$, SO$_3$N(R1)$_4$, H

PROCESS TO ACTIVATE SULFATED POLYSACCHARIDES

This application generally relates to processes to activate sulfated polysaccharides and particularly relates to a high-yield chemical process to efficiently activate biologically useful sulfated mucopolysaccharides where the activated mucopolysaccharide may then be attached to suitable polymeric, composite or metallic surfaces in order to provide biocompatible materials which may directly contact tissues, blood or blood products.

BACKGROUND

Surfaces of medical devices that are in direct contact with biological materials, such as tissues, blood and blood products, have been treated with surface modifying agents in order to make the contacting surfaces compatible with these types of sensitive biological materials. Sulfated polysaccharides have been used in a variety of applications to make biocompatible medical surfaces. For example, the blood contacting surfaces of devices such as blood oxygenators, blood pumps, catheters, or connection tubes and tubing may be treated with biologically active polysaccharides, particularly heparin or heparin derivatives, to make the surfaces of such devices nonthrombogenic and thus prevent clotting or clot formation related to surface contact with blood or blood products.

Several methods for specifically attaching or binding heparin or heparin derivatives to substrate surfaces have been reported. U.S. Pat. Nos. 4,613,665 and 4,810,784 report a process to attach heparin to different types of substrates. The reported process degrades a polysaccharide antithrombogenic agent, such as heparin, with nitrous acid to give fragments which react with primary amino groups on the substrate's surface to form intermediate Schiffs base conjugates. Reduction of the intermediate conjugates then covalently binds the fragments to the support.

In addition, U.S. Pat. No. 4,565,740 reports a substrate modified to include degraded heparin fragments where the substrate is initially treated with a polyamine and a dialdehyde crosslinker, then treated with dextran sulfate, further treated with a polyamine and finally treated with degraded heparin and sodium cyanoborohydride to chemically bind the heparin fragments to the polyamine. Similarly, U.S. Pat. No. 5,049,403 reports a substrate modified to include degraded heparin fragments where the substrate is initially treated with a polyamine that is crosslinked with crotonaldehyde.

Further, U.S. Pat. No. 4,326,532 reports a layered substrate coated with chitosan that reacts with an antithrombotic agent such as heparin. Specifically, heparin is condensed with a layer of chitosan that is initially applied to an acid oxidized or plasma etched hydrophobic substrate and, if needed, the condensed heparin is then reduced using sodium cyanoborohydride.

Alternative methods of modifying surfaces with activated heparin have also been reported. For example, U.S. Pat. Nos. 4,720,512 and 4,786,556 report activating heparin with sodium periodate, reacting the periodate-activated heparin with an amine-containing material to form a conjugate and then reducing the conjugate using sodium cyanoborohydride.

Besides various heparin activation and chemical bonding methods, other processes have been used to fix or attach heparin to substrates without actually chemically bonding heparin to the substrate. For example, U.S. Pat. No. 4,871,357 reports an ionic binding of heparin to surfaces using quaternary ammonium salts. Subsequent irradiation of ionically bound heparin using quaternary ammonium salts has been reported to covalently bond heparin to the surface. See, e.g., International Application No. PCT/US92/07661 published Apr. 1, 1993.

In spite of the many approaches to modify surfaces with biologically useful agents, a need exists for an efficient, effective process to prepare such modified surfaces which uses reagents which are easy to handle and are not toxic or hazardous to use. Polysaccharides are particularly difficult to work with because these polymers are generally not soluble in organic solvents and thus are not readily used with many common reaction methodologies. Thus, a preferred process would be carried out in an aqueous system.

Furthermore, the biological activity of active polysaccharides may be very sensitive to processing conditions. A desirable process would allow binding biologically active polysaccharides, such as heparin, to surfaces without degrading or otherwise altering the biological activity of the active polysaccharide when it is used to modify the surface of a substrate. A need exists for a process which may be adapted for use with many different types of active polysaccharides and substrates and which does not result in degradation or alteration of the biological activity of the active polysaccharide.

SUMMARY OF THE INVENTION

The present invention is directed to a novel, high-yield, efficient process to prepare an activated sulfated polysaccharide which may then be used in subsequent reactions or processes to bind the activated polysaccharide with a nucleophilic agent or an aminated surface. A preferred activation process comprises the steps of i) forming a polysaccharide tetraalkylammonium salt by contacting an aqueous mixture of a sulfated polysaccharide salt with an acid source such as a cation exchange resin to give a polysaccharide free acid followed by contacting the polysaccharide free acid with a tetraalkylammonium hydroxide to give the polysaccharide tetraalkylammonium salt, and then ii) forming an activated sulfated polysaccharide e.g. by contacting the polysaccharide tetraalkylammonium salt of step i) with a coupling reagent in an aprotic organic solvent at ambient temperatures for a period of time sufficient to form the activated sulfated polysaccharide. The activated sulfated polysaccharide of this invention may be used in further processing steps in commonly used organic reactions using aqueous mixtures or common organic solvents and conventional reaction conditions.

A variety of different sulfated polysaccharides may be activated using this invention. Those of ordinary skill in the art will recognize that sulfated polysaccharides or derivatives thereof are complex polymeric moieties as well as mixtures of such polymers. For example, heparin principally includes both one major and one minor polymeric moiety which are schematically represented by Formula A, the major structure, and Formula B, the minor structure.

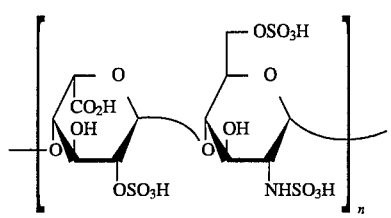

Formula A

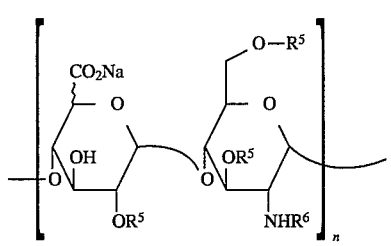

Formula B

In Formulas A and B, the variables are defined as follows: n is an integer, $R^5$ is a moiety —$SO_3Na$ or —H and $R^6$ is a moiety —$COCH_3$, —$SO_3Na$ or —H. Typically, the ratio of the major polymeric structure of heparin to the minor polymeric structure of heparin is about 85:15.

Suitable sulfated polysaccharides or polysaccharide derivatives which may be used in the present process include known biologically active polysaccharides such as heparin, heparan sulfate, chondroitin sulfate, dermatan sulfate, dextran sulfate, fucoidin sulfate, and keratan sulfate.

A preferred acid source for use in the first step of this process is an acidic cation exchange resin or membrane. Such resins or membranes are advantageous because they are available in solid form, may be used in ion exchange columns, and do not exude toxic and/or volatile fumes.

Suitable tetraalkylammonium hydroxides for use in the invention include ammonium hydroxides either with symmetrical tetraalkylammonium groups, e.g., tetrabutylammonium hydroxide, or with unsymmetrical ammonium groups, e.g., tributylethylammonium hydroxide. The alkyl groups are generally straight or branched chain alkyl groups of one to six carbon atoms. The preferred cyanating reactions may be carried out under conventional reaction conditions for cyanogen halides at temperatures of about −10° to 30° C.

Preferred coupling reagents include cyanating reagents such as cyanogen halides, p-nitrophenyl cyanate, N-cyanotriethylammonium tetrafluoroborate and 1-cyano-4-dimethylaminopyridinium tetrafluoroborate as well as other known coupling reagents such as disuccinimydyl carbonates, toluenesulfonyl chloride, tresyl chloride, carbonyl diimidazoles, 2-fluoro-1-methylpyridiniumtoluene-4-sulfonate and derivatives thereof. Typically, the preferred cyanating agents are used in the presence of an inorganic base such as sodium hydroxide or sodium carbonate or an organic base such as an amine. A particularly preferred cyanating reagent is a mixture of a cyanogen halide and an excess, e.g., about a 10% molar excess, of a trialkylamine in an aprotic organic solvent.

In another embodiment, this invention provides a process to bind or couple a sulfated polysaccharide to a nucleophilic agent. This process comprising the steps of i) forming a polysaccharide tetraalkylammonium salt by contacting an aqueous mixture of a sulfated polysaccharide salt with an acid source such as a cation exchange resin to give a polysaccharide free acid followed by contacting the polysaccharide free acid with a tetraalkylammonium hydroxide to give the polysaccharide tetraalkylammonium salt, and then ii) forming an activated polysaccharide by contacting the polysaccharide tetraalkylammonium salt of step i) with a coupling reagent in an aprotic organic solvent at ambient temperatures for a period of time sufficient to form the activated sulfated polysaccharide, and iii) contacting the activated polysaccharide with a nucleophile for a period of time sufficient to bind or couple the nucleophile to the activated polysaccharide. The nucleophile typically is used as a solution or mixture in a suitable solvent such as water or commonly used organic solvents. Suitable nucleophilic agents for use in this process include primary and secondary amines, including aminated polymers, or thiols.

Similarly, this invention provides a process to couple a biologically active, sulfated polysaccharide or derivative thereof to at least one exposed surface of a suitable support such as a polymeric of metal substrate or support. The steps of this embodiment comprise i) contacting at least one exposed surface of a support such as a polymeric support with a water-soluble aminated polymer at ambient temperatures for a period of time sufficient to give a primed surface, and ii) contacting the primed surface with a reactive biologically active polysaccharide in which the reactive biologically active polysaccharide is prepared by the polysaccharide activation process described above.

Preferred aminated polymers or primers include polyalkylene amines such as polyethyleneimine or polyethyleneimine crosslinked with suitable difunctional agents such as dialdehydes, acroleins, diepoxides or divinylsulfones. Suitable polyalkylene amines will have a molecular weight between 1,000 and 100,000. Suitable polymeric substrates for use in this embodiment include polyamides, polyurethanes, polyvinyl alcohols, polysulfones, nylons, polyvinyl chlorides, polyalkylenes such as polyethylenes and polypropylenes, celluloses, poly(meth)acrylates, polycarbonates, fluoropolymers such as poly(tetrafluoroethylene), silicones or polyesters such as polyethylene terephthalate, as well as other materials which have been used in known medical devices such as glass, stainless steel and titanium.

Polymeric, metallic or composite materials having utility in the present invention include solid organic polymers, glass and metals in the form of shaped articles, powders, granules, pellets, films, fibers or foams. Preferably, such polymeric, metallic or composite materials are biomaterials in the form of medical devices used for in vivo, ex-vivo, and in vitro diagnostic and therapeutic procedures. Examples of these devices include blood contacting medical devices such as vascular grafts, catheters, cannulas, stents, indwelling blood monitoring devices, artificial kidneys, artificial heart-lungs, extracorporeal circuits for auxiliary circulating devices, A-V shunts, artificial heart valves, temporary blood by-pass tubes, and dialysis membranes.

An alternative embodiment of this invention is related to the process using an aminated polymer to prime a surface. In this embodiment, however, the surface of a polymeric support is mechanically primed to provide a surface containing nucleophilic groups using known etching processes such as chemical or plasma etching as described, for example, in U.S. Pat. No. 4,326,532. After the surface of the polymeric support has been etched or primed, an activated polysaccharide prepared by the present process is contacted with the mechanically primed surface.

BRIEF DESCRIPTION OF THE DRAWINGS

FIG. 3 is a schematic representative of the steps used to couple a sulfated polysaccharide such as activated heparin represented by Formulas 7 and 8 to a primed surface.

DETAILED DESCRIPTION

Figure 1:
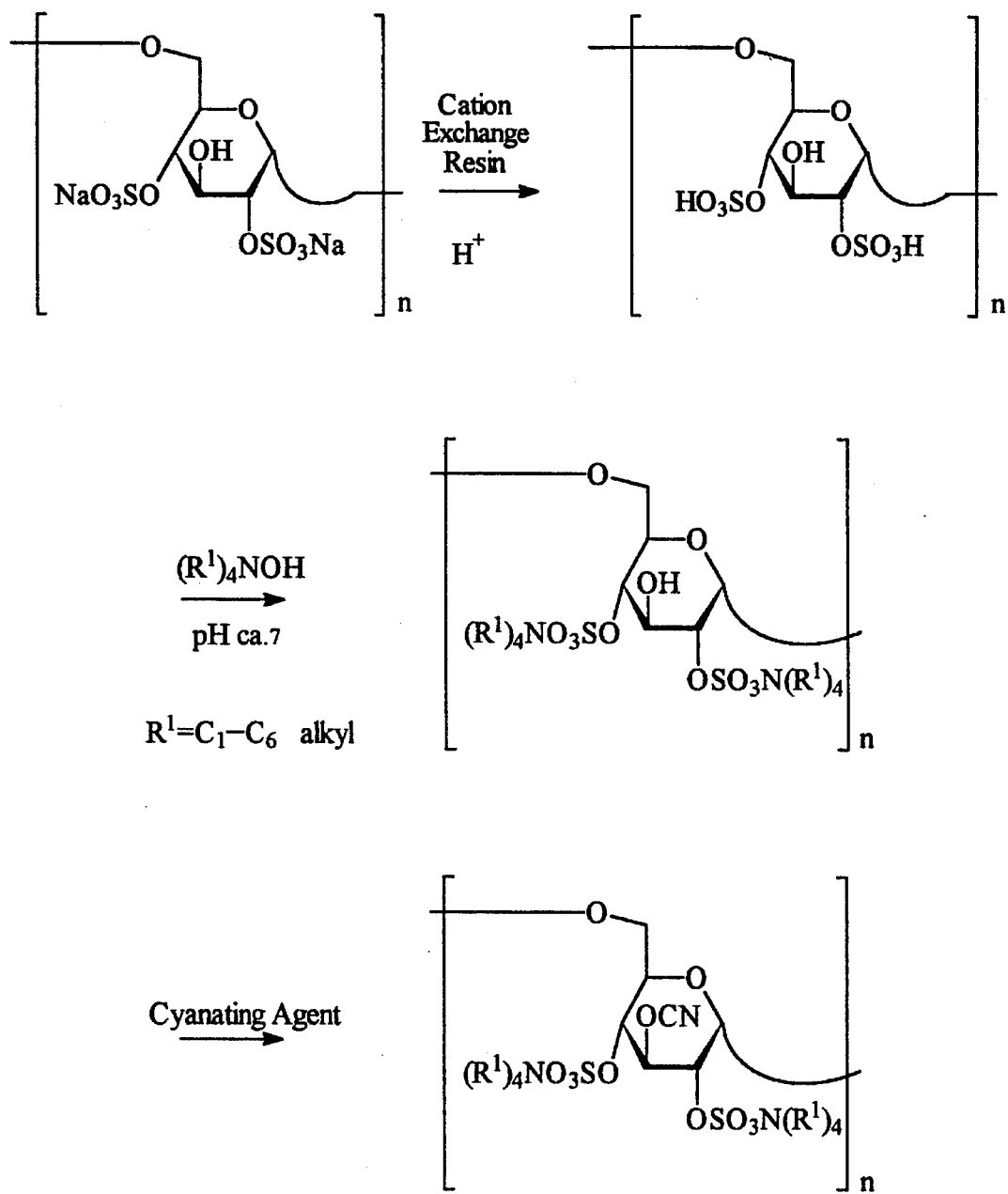
FIG. 1 is a schematic representation of the steps used to activate dextran sulfate with a coupling reagent.
Figure 2:
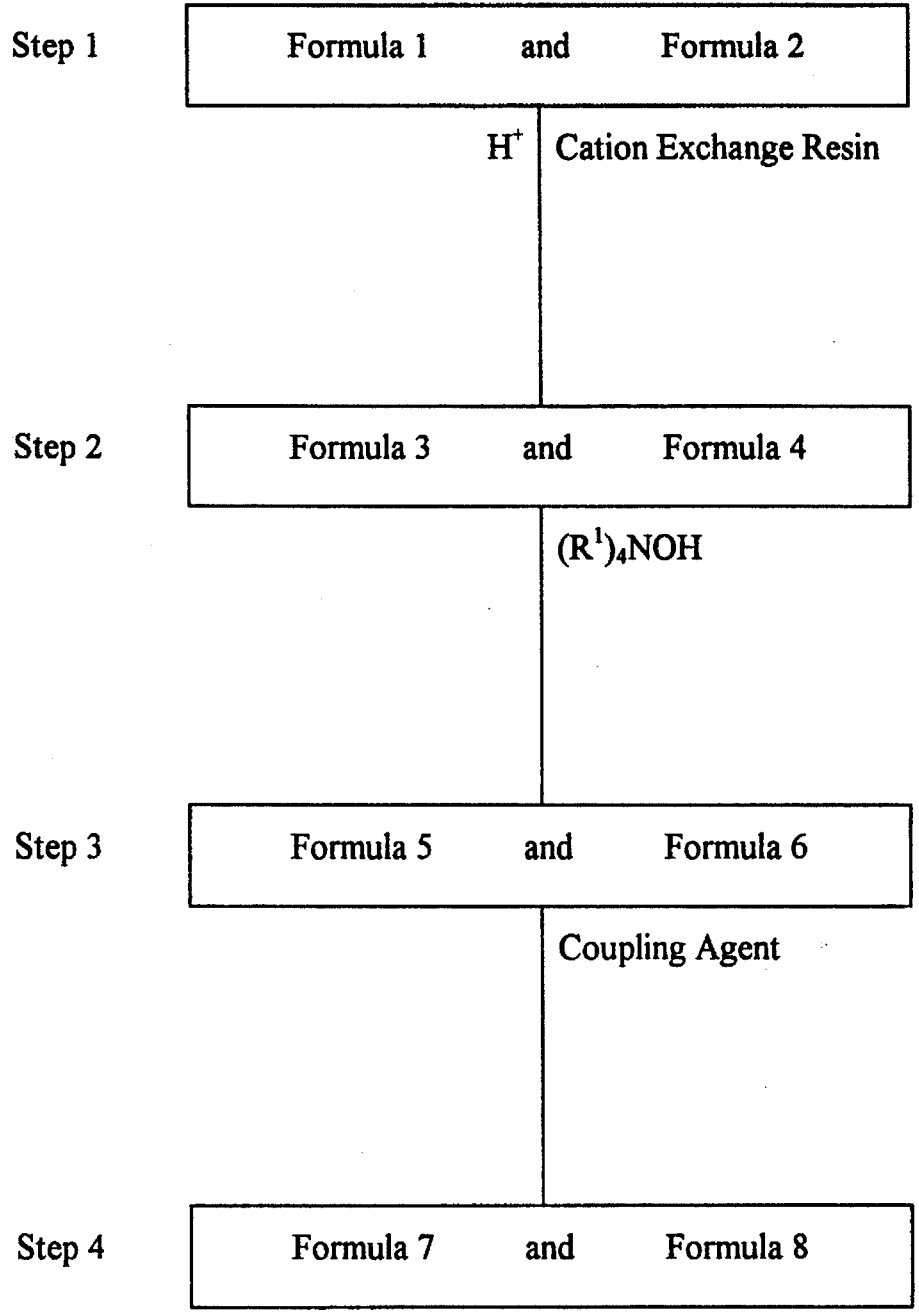
FIG. 2 is a schematic representation of the steps used to activate heparin represented by Formulas 1 and 2 with a coupling reagent.
Figure 4A:
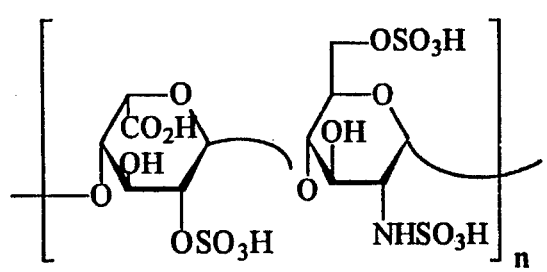
FIGS. 4a–4c are structural representations of polysaccharide derivatives of Formulas 1–11.
Figure 4A:
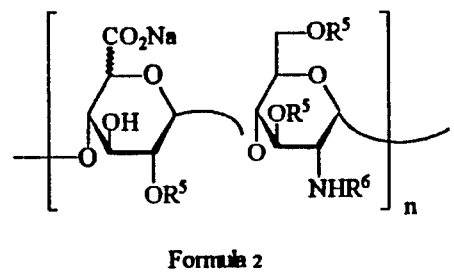
Figure 4A:
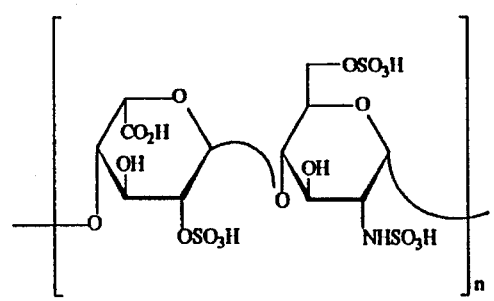
Figure 4A:
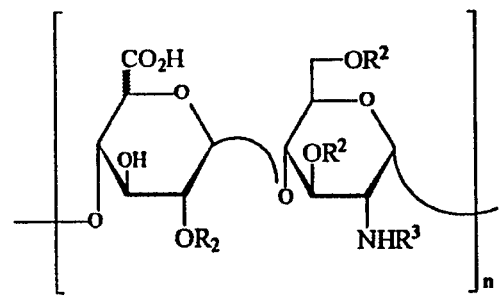
Figure 4B:
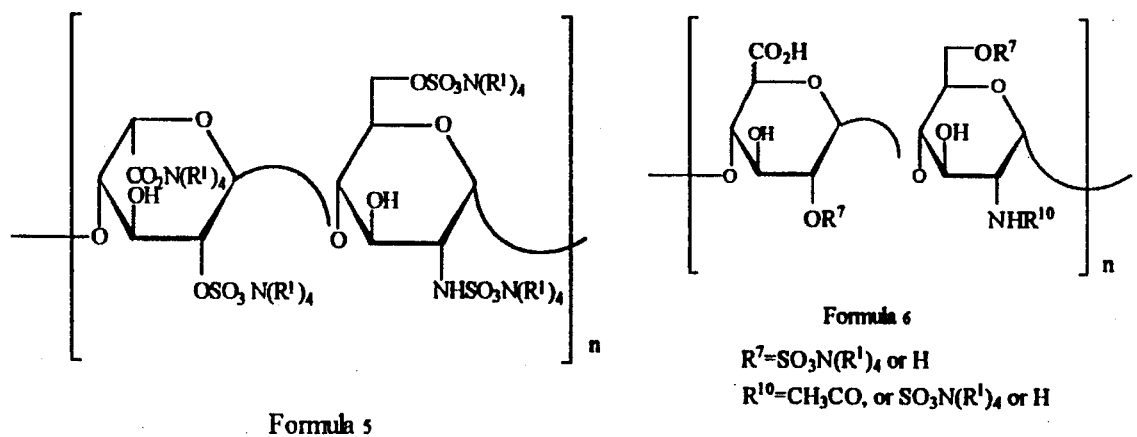
Figure 4B:
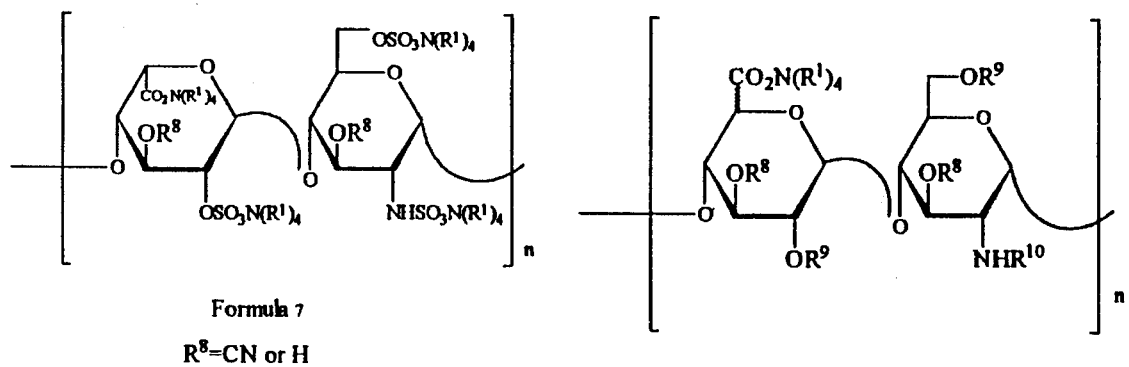
Figure 4C:
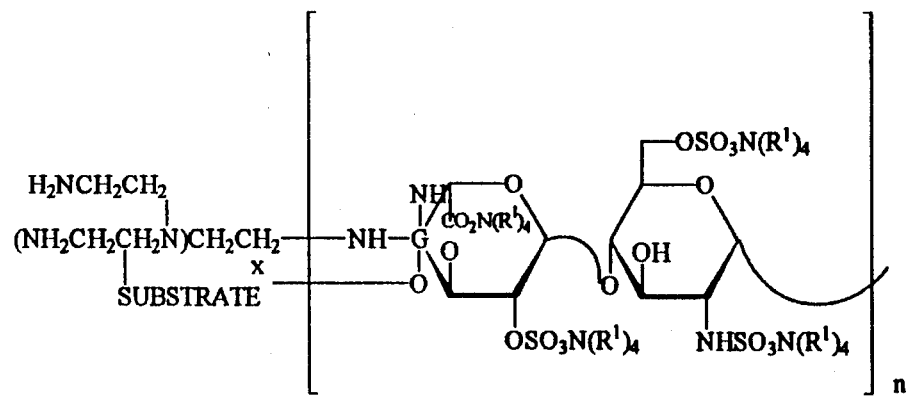
Figure 4C:
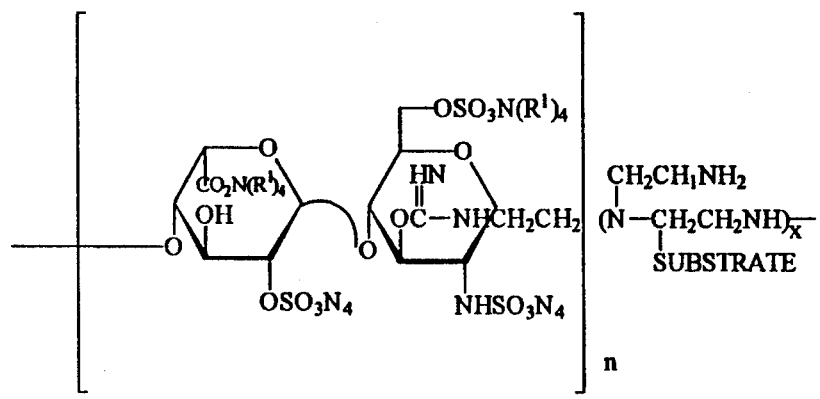
Figure 4C:
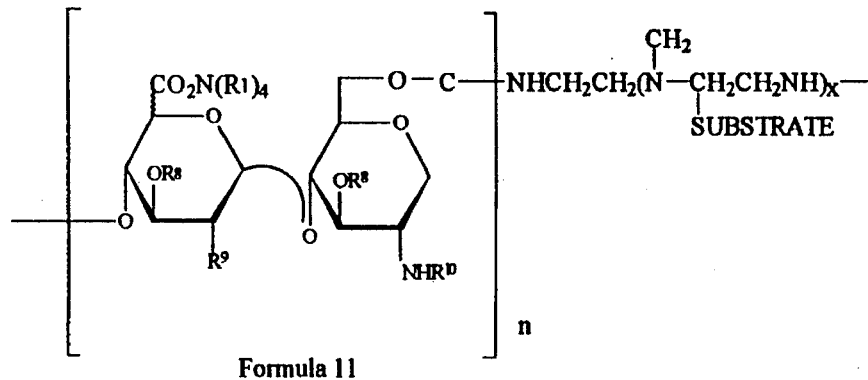

The present invention provides a high-yield, efficient process to activate polysaccharides and then use the activated polysaccharide to bind to nucleophilic agents or to the surfaces of materials used to make medical devices which contact tissues, blood or blood products. The present activation process is readily described as occurring in two separate steps although it is not necessary to perform an isolation or purification process between the two steps. In the first step, an aqueous mixture of a sulfated polysaccharide is contacted with an acid source such as a cation exchange resin or membrane to form a polysaccharide free acid which is an intermediate acidified derivative of the polysaccharide. A readily used resin is a macroporous cationic ion exchange resin such as AMBERLITE IR 120 resin (commercially available from Aldrich Chemical Co., Milwaukee, Wis.). When a cationic ion exchange resin is used, the aqueous polysaccharide mixture may be simply passed through a short column of the resin, and the resin then rinsed with deionized water.

The intermediate acidified polysaccharide is then immediately quenched with an alcoholic mixture such as a methanolic mixture of a tetraalkylammonium hydroxide at ambient temperatures to give a polysaccharide tetraalkylammonium salt. The quenching process may be readily monitored using a pH electrode in the mixture as the tetraalkylammonium hydroxide is added to the acidified polysaccharide. The resulting polysaccharide tetraalkylammonium salt at neutral pH values, preferably at a pH value of about 7, is soluble in polar organic solvents and may be isolated, if desired, by evaporative removal of the solvent such as methanol and then freeze drying the remaining aqueous mixture.

In a second step, the polysaccharide ammonium salt is converted into an activated agent using a suitable coupling agent, preferably a cyanating agent, in an aprotic polar organic solvent such as acetonitrile, N,N-dimethylformamide, dimethylsulfoxide or N,N-dimethylacetamide. Suitable cyanating reagents include cyanogen halides, preferably cyanogen chloride or cyanogen bromide, in combination with trialkylamines such as triethylamine. When used in a preferred embodiment of the present process, a mixture of cyanogen bromide and acetonitrile is added to a mixture of the polysaccharide ammonium salt in acetonitrile followed by the addition of a mixture of triethylamine in acetonitrile. When the mixture of triethylamine is initially added to the polysaccharide ammonium salt and cyanogen bromide, a precipitate briefly forms which then redissolves within a few minutes after the addition to provide a homogeneous mixture of the activated polysaccharide. Initial stability studies have demonstrated that the activated polysaccharide may be stored for several weeks at −4° C.

In the present invention the activated polysaccharide will readily couple with, i.e., react or coat onto, a suitable substrate or solid support by reaction of the activated polysaccharide site with a nucleophilic group, which is either attached to, associated with, or is actually a component of the substrate. This nucleophilic group will generally be an amino or thiol group which is part of a suitable polymer. Preferred polymers are aminated polymers such as polyethyleneimine which may be further crosslinked on the substrate using known processes, if desired. Suitable polyethyleneimine based polymers for use in this invention are well known and are described, e.g., in U.S. Pat. No. 4,565,745 or are commercially available, such as Polymin SN and Polymin P available from BASF, Nalco 7134 available from Nalco Chemical Company, or polyethyleneimine available from Aldrich Chemical Company.

EXAMPLES

The following examples are provided to further illustrate the practice of the present invention. The examples are not intended to limit the invention which is defined in the appended claims.

In the examples, the surface-bound concentration of heparin may be measured by a thrombin inhibition assay. The inhibition assay exploits the observation that thrombin enzymatically cleaves a commercially available synthetic substrate (S-2238) to yield a product whose concentration is proportional to its absorbance at 405 nm, and the rate of formation of product is therefore proportional to a thrombin concentration. Decreased amounts of product reflect inhibition of thrombin by heparin in the presence of excess amounts of antithrombin-III. Briefly, the assay is performed by adding, in the following sequence, the listed materials to test tubes: 0.05 ml of an unknown sample and 0.05 ml of buffer (where the sample has an unknown concentration of heparin on the surface), or 0.05 ml of a standard heparin solution, 1.0 ml of 0.3 mM S-2238, 0.1 ml of antithrombin-III (5 units/ml), and 0.1 ml of thrombin (0.1 units/ml). The standard heparin solutions (50 microliters) contain, for example, 0.08, 0.04, 0.02, 0.01 and 0.0 micrograms of heparin. The assay is carried out at 37° C. with overnight incubation in a water bath, with continuous mixing. Measurements are made on 0.20 ml aliquots taken from the unknown and standard solutions using microtiter plates and optical density at 405 nm is recorded. The optical density values are related to heparin concentration using the heparin standard solutions.

More specifically, the assay procedure is a modification of Chandler et al., *J. Biomed. Mater. Res.* 22:497–508 (1988) which uses the following reagents.

| Reagent | Manufacturer | Concentration |
| --- | --- | --- |
| Antithrombin-III | Sigma | 5 units/ml |
| S-2238 | Kabi | 0.3 mM |
| Thrombin | Sigma | 5 units/ml |
| Hanks' Buffer | Sigma | 0.1 units/ml |
| Heparin | Sigma | 10 units/ml |

Antithrombin-III is reconstituted to 5 units/ml with 10 ml deionized distilled water and refrigerated at 4° C. S-2238 is reconstituted to 0.3 mM using 133 ml of buffer stock solution of PBS (phosphate buffered saline) with 1 mg/ml BSA (bovine serum albumin, Cat. No. A7838, Sigma Chemical Company, St. Louis, Mo.) and 1 mg/ml polyethylene glycol (8000MW, Cat. No. P2139, Sigma Chemical Company, St. Louis, Mo.) and stored at 4° C. Thrombin is reconstituted to 10 units/ml with 10 ml Hanks' phosphate buffered saline and stored at −20° C. in 1 ml aliquots. A 1:100 dilution of thrombin is used in the assay.

Standard heparin solutions are prepared from the 10 units/ml stock solution by serial dilution. Each new batch of thrombin and/or heparin must be tested to insure maximum sensitivity. Representative values of standard heparin solutions are listed in the following table.

| Standard | Concentration |
|---|---|
| 1 | .08 µg/50 µl |
| 2 | .04 µg/50 µl |
| 3 | .02 µg/50 µl |
| 4 | .01 µg/50 µl |
| 5 | 0 µg |

To measure absorbance, 0.05 ml of appropriate standards as well as an unknown sample having a measured surface area together with PBS/BSA buffer (0.05 ml) are dispensed into tubes. The following reagents are added to each of the tubes, 0.1 ml antithrombin-III, 1.0 ml S-2238 and 0.1 ml thrombin, all tubes are vortexed and then incubated overnight at 37° C. After incubation, 0.2 ml from each tube is added to a well of a microtiter plate in duplicate for each tube and optical density readings are taken at 405 nM. (All standards and samples are run in duplicate, with duplicate optical density readings at 405 nM.)

EXAMPLE 1

Multi-Step Preparation of Reactive Polysaccharides

Step 1. Preparation of tetrabutyl ammonium salt of heparin:

Ten grams of heparin, sodium salt was dissolved in 100 g of deionized water. This solution was passed through 35 g of AMBERLITE IR 120 cation exchange resin in the acid form in a 2.8 cm diameter column. The column was rinsed through with an additional 150 g of deionized water. The effluent was collected in the beaker with a magnetic bar and pH electrode, and the effluent was neutralized to a pH value of about 7 with a 25% solution of tetrabutyl ammonium hydroxide solution in methanol as it was being collected. 38 g of the tetrabutyl ammonium hydroxide solution was used. The methanol was stripped under a water aspirator vacuum with a rotary evaporator, and the solution freeze dried to yield 20.5 g of tetrabutyl ammonium heparin as a white solid.

Step 1a. Preparation of tetrabutyl ammonium dextran sulfate:

Four grams of dextran sulfate was dissolved in 40 cc of deionized water. This solution was passed through 50 ml of AMBERLITE IR 120 cation exchange resin in a 3.5 cm diameter column. The effluent was neutralized to a pH value of about 7 with 16.5 g of 25% tetrabutyl ammonium hydroxide in methanol. The methanol was stripped off with a rotary evaporator and the residue was freeze-dried to yield 9.5 g of tetrabutyl ammonium dextran sulfate.

Step 2. Activation of tetrabutyl ammonium heparin:

Tetrabutyl ammonium heparin was dissolved in acetonitrile to make a 100 mg/ml solution. To 5.0 ml of this solution in an ice bath was added 5.0 ml of a 100 mg/ml solution of cyanogen bromide in acetonitrile. To this solution was added 6.0 ml of a 100 mg/ml solution of triethylamine in acetonitrile. The reaction mixture became immediately cloudy with the last addition of base which then clarified within a few minutes. This solution has remained active after two weeks of storage at −4° C.

Step 2a. Activation of tetrabutyl ammonium dextran sulfate:

To 1.3 ml of a 100 mg/ml solution of tetrabutyl ammonium dextran solution in methanol cooled with an ice bath was added 0.26 ml of a 5M solution of cyanogen bromide in acetonitrile. To this solution was added 1.3 ml of a 100 mg/ml solution of triethylamine in acetonitrile. The reaction mixture became cloudy immediately with the last addition which clarified within a few minutes.

Step 3. Attachment of activated heparin to a substrate:

Plastic polycarbonate strips were dipped in a 5 mg/ml solution of poly(ethylenimine) solution in deionized water, then rinsed in deionized water. These primed strips were immersed in a solution of a 1:10 dilution of the activated tetrabutyl ammonium heparin solution from Step 2. in pH 3.5, 0.1M sodium phosphate solution at room temperature for about one hour. The coated polycarbonate strip was rinsed for 10 minutes in 25% saline to remove ionically bound heparin, then subjected to thrombin inhibition assay. The results showed heparin activity of about 0.1 µg/cm$^2$ after 20 minutes and about 0.16 µg/cm$^2$ after one hour.

Step 3a. Attachment of activated dextran sulfate to a substrate:

Plastic polycarbonate strips were dipped in a 5 mg/ml solution of poly(ethylenimine) solution in deionized water, then rinsed in deionized water. These primed strips were immersed in a solution of a 1:10 dilution of the activated tetrabutyl ammonium dextran sulfate solution from Example 2a. in pH 7 phosphate buffered saline at 50° C. for 20 min. The coated polycarbonate strip was rinsed for 10 minutes in 25% saline to remove ionically bound dextran sulfate. This strip gave a violet color when stained with a toluidine blue solution to verify the presence of the negatively charged sulfate groups of tetrabutyl ammonium dextran sulfate.

EXAMPLE 2

Heparin Coated Articles

External surfaces of polycarbonate (sold under the tradename HYZOD by Sheffield Plastics Inc., Sheffield, Mass.) sheets cut into strips as well as external surfaces of extracorporeal centrifugal pumps (made of polycarbonate and poly(methyl methacrylate), Model 7850, Sarns/3M, Ann Arbor, Mich.), were immersed in a 0.1 wt. % polyethyleneimine (PEI) solution (0.40 g PEI in 400 ml distilled water, PEI having an average molecular weight of 50,000 commercially available from Aldrich Chemical Company, Milwaukee, Wis.) at room temperature for fifteen minutes. The polycarbonate strips and pumps were then removed from the PEI solution and rinsed thoroughly with distilled water. The polycarbonate strips and pumps were next immersed in a 0.03 wt. % dextran sulfate (DS) solution (0.15 g DS in 500 ml pH 3.9 citrate buffer prepared by mixing 11.0 g citric acid monohydrate and 9.0 g sodium chloride in one liter distilled water and adjusting the pH to 3.9 with 5N sodium hydroxide, DS having an average molecular weight of 500,000 commercially available from Sigma Chemical Company, St. Louis, Mo.) at room temperature for five minutes. Again, the polycarbonate strips and pumps were rinsed thoroughly with water and then re-immersed in a 0.1 wt. % polyethyleneimine solution at room temperature for fifteen minutes.

The now primed polycarbonate strips and pumps were then exposed to an activated heparin solution heated to a temperature of 50° C. for ten minutes. The activated heparin solution was prepared by mixing 0.5 g heparin tetrabutyl ammonium salt prepared according to the process of Example 1, 50 ml acetonitrile, 10 ml 5M cyanogen bromide in acetonitrile (commercially available from Aldrich Chemical Company, Milwaukee, Wis.) and 55 ml 10 wt. % triethylamine in acetonitrile. This mixture was stirred at room temperature for about two hours to yield a homogeneous solution. After exposure to the activated heparin solution, the polycarbonate strips and pumps were rinsed thoroughly with distilled water, immersed in a 25 wt. % sodium chloride solution at room temperature for five minutes and finally rinsed again with distilled water.

After the surfaces of the polycarbonate strips and pumps were primed and coated with heparin the heparin activity of the coated surfaces was assayed using the thrombin inhibition assay described above. This assay demonstrated that the heparin activity on the heparin coated articles was about about 0.09 µg/cm$^2$.

We claim:

1. A process to prepare an activated sulfated polysaccharide comprising the steps of
    i) forming a polysaccharide tetraalkylammonium salt by contacting an aqueous mixture of a sulfated polysaccharide salt with a cation exchange resin to give a polysaccharide free acid and then contacting the polysaccharide free acid with a tetraalkylammonium hydroxide to give the polysaccharide tetraalkylammonium salt, and
    ii) forming an activated sulfated polysaccharide by contacting the polysaccharide tetraalkylammonium salt of step i) with a coupling reagent in an aprotic organic solvent at a temperature of about −10° to 30° C. for a period of time sufficient to form the activated sulfated polysaccharide.

2. The process of claim 1 wherein step ii) occurs in about 5–30 minutes at a temperature of about 0°–30° C.

3. The process of claim 1 wherein the coupling reagent is a cyanating reagent selected from the group consisting of cyanogen halides, p-nitrophenyl cyanate, N-cyanotriethylammonium tetrafluoroborate and 1-cyano-4-dimethyl amino pyridinium tetrafluoroborate.

4. The process of claim 1 wherein the cyanating reagent is a mixture of cyanogen bromide and a trialkylamine in an aprotic organic solvent.

5. The process of claim 1 wherein the polysaccharide salt is selected from the group consisting of heparin, heparan sulfate, chondroitin sulfate, dermatan sulfate, dextran sulfate, fucoidin sulfate, keratan sulfate and physiologically acceptable salts thereof.

6. The process of claim 1 wherein the aprotic organic solvent in step ii) is acetonitrile.

7. A process to couple an activated sulfated polysaccharide to a nucleophile comprising the steps of
    i) forming a polysaccharide tetraalkylammonium salt by contacting an aqueous mixture of a sulfated polysaccharide salt with a cation exchange resin to give a polysaccharide free acid and then contacting the polysaccharide free acid with a tetraalkylammonium hydroxide to give the polysaccharide tetraalkylammonium salt, and
    ii) forming an activated sulfated polysaccharide by contacting the polysaccharide tetraalkylammonium salt of step i) with a coupling reagent in an aprotic organic solvent at ambient temperatures for a period of time sufficient to form the activated sulfated polysaccharide, and
    iii) contacting the activated polysaccharide with a nucleophile in a solvent for a period of time sufficient to couple the nucleophile to the polysaccharide.

8. The process of claim 7 wherein the polysaccharide salt is selected from the group consisting of heparin, heparan sulfate, chondroitin sulfate, dermatan sulfate, dextran sulfate, fucoidin sulfate, keratan sulfate and physiologically acceptable salts thereof.

9. The process of claim 7 wherein the nucleophile is selected from the group consisting of primary amines, secondary amines, aminated polymers, and thiols.

10. A process to couple a biologically active sulfated polysaccharide or derivative thereof to at least one exposed surface of a polymeric support comprising the steps of
    i) contacting at least one exposed surface of a polymeric support with a water-soluble aminated polymer at ambient temperatures for a period of time sufficient to give a primed surface, and
    ii) contacting the primed surface with a solution of a reactive biologically active polysaccharide wherein the reactive biologically active polysaccharide is prepared by a process comprising the steps of
        a) forming a polysaccharide tetraalkylammonium salt by contacting an aqueous mixture of a sulfated polysaccharide salt with a cation exchange resin to give a polysaccharide free acid and then contacting the polysaccharide free acid with a tetraalkylammonium hydroxide to give the polysaccharide tetraalkylammonium salt, and
        b) forming an activated sulfated polysaccharide by contacting the polysaccharide tetraalkylammonium salt of step a) with a coupling reagent in an aprotic organic solvent at ambient temperatures for a period of time sufficient to form the activated sulfated polysaccharide.

11. The process of claim 10 wherein the polysaccharide salt is selected from the group consisting of heparin, heparan sulfate, chondroitin sulfate, dermatan sulfate, dextran sulfate, fucoidin sulfate, keratan sulfate and physiologically acceptable salts thereof.

12. The process of claim 10 wherein the aminated polymer is polyethyleneimine.

13. The process of claim 10 wherein the polymer is selected from the group consisting of polyamides, polycarbonates, polyvinyl chlorides, polyalkylenes, poly(meth)acrylates, polyesters, polyvinyl alcohols, polyurethanes, fluoropolymers and silicones.

14. A process to couple a biologically active, sulfated polysaccharide or derivative thereof to at least one exposed surface of a polymeric support comprising the steps of
    i) chemically modifying at least one exposed surface of a polymeric support for a period of time sufficient to give a modified surface containing nuceophilic groups, and
    ii) contacting the modified surface with a solution of a reactive biologically active polysaccharide wherein the reactive biologically active polysaccharide is prepared by a process comprising the steps of
        a) forming a polysaccharide tetraalkylammonium salt by contacting an aqueous mixture of a sulfated polysaccharide salt with a cation exchange resin to give a polysaccharide free acid and then contacting the polysaccharide free acid with a tetraalkylammonium hydroxide to give the polysaccharide tetraalkylammonium salt, and b) forming an activated sulfated polysaccharide by contacting the polysaccharide tetraalkylammonium salt of step a) with a coupling reagent in an aprotic organic solvent at ambient temperatures for a period of time sufficient to form the activated sulfated polysaccharide.

15. The process of claim 14 wherein the polymeric support is modified by chemical or plasma etching of an exposed surface thereof.

* * * * *